US006465219B1

(12) United States Patent
Zhu

(10) Patent No.: US 6,465,219 B1
(45) Date of Patent: Oct. 15, 2002

(54) POLYNUCLEOTIDE POOLS ENRICHED IN EITHER HIGH-ABUNDANCE OR LOW-ABUNDANCE SEQUENCES

(75) Inventor: York Yuan-Yuan Zhu, Sunnyvale, CA (US)

(73) Assignee: Genemed Biotechnologies, Inc., South San Francisco, CA (US)

( * ) Notice: Subject to any disclaimer, the term of this patent is extended or adjusted under 35 U.S.C. 154(b) by 0 days.

(21) Appl. No.: 09/632,898

(22) Filed: Aug. 7, 2000

(51) Int. Cl.[7] ........................... C12P 19/34; C12Q 1/68; C07H 21/04
(52) U.S. Cl. .................. 435/91.1; 435/6; 435/91.2; 536/23.1; 536/24.5
(58) Field of Search .................. 435/6, 91.2, 91.1; 536/23.1, 24.5

(56) References Cited

U.S. PATENT DOCUMENTS

| | | | |
|---|---|---|---|
| 5,436,149 A | 7/1995 | Barnes | 435/194 |
| 5,512,462 A | 4/1996 | Cheng | 435/91.2 |
| 5,514,545 A * | 5/1996 | Eberwine | 435/6 |
| 5,589,339 A | 12/1996 | Hampson | 435/6 |
| 5,591,575 A | 1/1997 | Hampson et al. | 435/6 |
| 5,712,127 A | 1/1998 | Malek et al. | 435/91.21 |
| 5,716,785 A | 2/1998 | Van Gelder et al. | 435/6 |
| 5,932,451 A | 8/1999 | Wang et al. | 435/91.21 |
| 5,958,738 A * | 9/1999 | Lindemann et al. | 435/91.2 |
| 5,962,272 A | 10/1999 | Chenchik et al. | 435/91.1 |

OTHER PUBLICATIONS

Wang, Z. et al., "A gene expression screen", PNAS vol. 88, pp. 11505–11509 (1991).*
Akowitz, Alfred and Manuelidis, Laura, "A novel CDNA/PCR strategy for efficient cloning of small amounts of undefined RNA," *Gene* 81:295–306 (1989).
Bertioli, D.J. et al., "Method Based on PCR for the Construction of cDNA Libraries and Probes From Small Amounts of Tissue," *Bio Techniques* 16: 1054–1058 (1994).
Bonaldo, Maria de Fatima et al., "Normalization and Subtraction: Two Approaches to Facilitate Gene Discovery," *Genome Research* 6:791–806 (1996).
Fire, Andrew et al., "Potent and specific genetic interference by double–stranded RNA in Caenorhabditis elegans," *Nature* 391:806–811 (Feb. 19, 1998).
Fromont–Racine, Micheline et al., "A Highly Sensitive Method for Mapping the 5' Termini of mRNAs," *Nucleic Acids Research* 21:1683–1684 (1993).
Marx, Jean, "Interfering With Gene Expression," *Science* 288:5470:1370–1372 (May 26, 2000).
Reeder, J.A. et al., "Expression of antisense CD44 variant 6 inhibits colorectal tum metastasis and tumor growth in a wound environment," *Cancer Research* 58:16:3719–26 (Abstract)(Aug. 15, 1988).
Sharp, Phillip A. et al., "Molecular Biology: RNA Interference," *Science* 287:5462:2431–2433 (Mar. 31, 2000).
Soares, Marcelo Bento et al., "Construction and Characterization of a Normalized cDNA Library," *Proc, Natl. Acad. Sci. USA* 91:9228–9232 (Sep. 1994).
Suzuki, Yutuka et al., "Construction and Characterization of a Full Length–enriched and a 5'–end–enriched cDNA Library," *Gene* 200:149–156 (1997).
Zhu, York et al., "Synthesis of High–Quality cDNA from Nanograms of Total of Poly A+RNA with the CapFinder™ PCR cDNA Library Construction Kit," *CLONTECHniques* 30–31 (Jul. 1996).

* cited by examiner

*Primary Examiner*—Kenneth R. Horlick
*Assistant Examiner*—Teresa Strzelecka
(74) *Attorney, Agent, or Firm*—Quine Intellectual Property Law Group, P.C.; Emily M. Haliday

(57) ABSTRACT

This invention provides novel methods for producing a plurality of polynucleotides prepared from a polynucleotide sample and the plurality of polynucleotides so produced. The plurality of polynucleotides is either substantially enriched in high-abundance polynucleotide sequences relative to the polynucleotide sample or substantially enriched in low-abundance polynucleotide sequences relative to the polynucleotide sample. Each of the polynucleotides in the plurality of polynucleotides includes a RNA promoter sequence and a universal primer site. The invention also provides kits useful in the methods of the invention and for using the pools of polynucleotides produced thereby. The polynucleotide pools are useful in a wide variety of applications, such as cloning, expression, and hybridization studies. Pools enriched in low-abundance polynucleotides are particularly useful in studies aimed at identifying important regulatory proteins.

50 Claims, No Drawings

POLYNUCLEOTIDE POOLS ENRICHED IN EITHER HIGH-ABUNDANCE OR LOW-ABUNDANCE SEQUENCES

FIELD OF THE INVENTION

This invention relates to methods and kits for selecting polynucleotide pools from a sample and the selected polynucleotide pools produced thereby. In particular, this invention provides a method for preparing a polynucleotide pool enriched in high-abundance sequences relative to the sample and a subtractive hybridization method for using such a polynucleotide pool to prepare a polynucleotide pool enriched in low-abundance sequences.

BACKGROUND OF THE INVENTION

Biologically active proteins have been the subject of intense research as candidates for therapeutic, diagnostic, and other applications. The first step is these efforts is typically the cloning of the gene encoding the protein from messenger RNA (mRNA). The mRNA of human and other mammalian cells can be divided into three frequency classes: (1) high-abundance sequences, which represent about 10–20% of the total mRNA population; (2) medium-abundance sequences, which represent about 40–45% of mRNA, and (3) low-abundance sequences, which represent another 40–45% of mRNA. Many genes encoding proteins with important regulatory functions, such as hormones and their receptors, are expressed at a low level and the corresponding transcripts fall into the low-abundance class of sequences.

Efforts to clone low-abundance sequences have employed normalized cDNA libraries in which the frequencies of all clones in the library are within a narrow range. However, this approach does not address the loss of low-abundance sequences in the process of generating the cDNA library, which preferentially replicates medium- and high-abundance sequences as well as shorter sequences. A method that facilitated the selection of a pool low-abundance polynucleotides from an mRNA population and that provided a means to produce large amounts of such sequences, without the losses that accompany cloning, would greatly assist research aimed at identifying important regulatory proteins. Ideally, such methods would be capable of replicating a broad range of transcripts without prior cloning into vectors and without requiring knowledge of sequence. Preferably, the low-abundance polynucleotides produced by such methods would be representative of the full-length transcripts (e.g., fill-length cDNA clones).

SUMMARY OF THE INVENTION

The invention provides a method for preparing a selected polynucleotide pool from a polynucleotide sample. In a preferred embodiment, the selected polynucleotide pool is enriched in one or more high-abundance polynucleotides relative to the polynucleotide sample. The method entails synthesizing first antisense polynucleotide strands from sense polynucleotides of, or prepared from, the polynucleotide sample using an antisense primer complex. The antisense primer complex includes an antisense primer operably linked to an RNA promoter sequence, such that the RNA promoter sequence is 5' of the antisense primer. Next, a universal primer site is added to the 3' ends of the first antisense polynucleotide strands. The resultant first antisense polynucleotide strands are then diluted to substantially eliminate at least some low-abundance first antisense polynucleotide strands. After dilution, first double-stranded polynucleotides are produced from the remaining first antisense polynucleotide strands. The first double-stranded polynucleotides are enriched in high-abundance polynucleotide sequences relative to the polynucleotide sample.

In a preferred embodiment of the method, the polynucleotide sample is an mRNA sample, the first antisense polynucleotide strands are first antisense cDNA strands, and the first double-stranded polynucleotides are first double-stranded cDNA molecules. The synthesis of first antisense cDNA strands can be primed using a random primer or an oligonucleotide-dT primer. The universal primer site can be added to the 3' end of the first antisense cDNA strands by template switching, oligonucleotide-tailing, or ligation. The RNA promoter sequence is conveniently one that is recognized by a bacteriophage RNA polymerase, such as T7, T3, or SP6 polymerase.

Preferably, the first double-stranded polynucleotides are produced by amplifying the first antisense polynucleotide strands remaining after dilution, and the amplification is carried out using a universal primer that hybridizes to the universal primer site as the 5' primer and using the antisense primer complex as the 3' primer. Most preferably, the amplification is performed by enhanced polymerase chain reaction. This reaction produces a pool of double-stranded polynucleotides that are enriched in high-abundance sequences relative to the original polynucleotide sample. The method optionally includes synthesizing first antisense RNA molecules from the first double-stranded polynucleotides. This pool of antisense RNA molecules is enriched in high-abundance sequences and can therefore be used as a "driver" in subtractive hybridization.

The invention also provides a method of using antisense polynucleotide strands, preferably the high-abundance-enriched antisense RNA molecules prepared as described above, to produce a selected polynucleotide pool from a polynucleotide sample. In a preferred embodiment, the selected polynucleotide pool is enriched in one or more low-abundance polynucleotides relative to the polynucleotide sample. The method entails hybridizing first antisense polynucleotide strands to sense polynucleotide strands of, or prepared from, a polynucleotide sample under hybridization conditions. Preferably, the molar ratio of the first antisense polynucleotide strands to the other polynucleotides in the hybridization mixture is between about 1 and about 100 to 1.

The resulting hybridization mixture includes unhybridized sense polynucleotide strands that are enriched in low-abundance polynucleotide sequences relative to the polynucleotide sample. Second antisense polynucleotide strands are synthesized from the unhybridized sense polynucleotide strands using an antisense primer or an antisense primer complex. The antisense primer complex includes an antisense primer operably linked to an RNA promoter sequence, such that the RNA promoter sequence is 5' of the antisense primer. An antisense primer complex is preferably employed if it is desirable to produce a pool of selected polynucleotides that each include an RNA promoter to facilitate the synthesis of antisense RNA from the selected polynucleotides.

Next, a universal primer site is added to the 3' ends of the second antisense polynucleotide strands. Second double-stranded polynucleotides are then produced from the second antisense polynucleotide strands. This pool of polynucleotides is enriched in low-abundance polynucleotide sequences relative to the polynucleotide sample.

In a preferred embodiment of the method, the polynucleotide sample is an mRNA sample, the sense polynucleotide strands are mRNA molecules, the second antisense polynucleotide strands are second antisense cDNA strands, and the second double-stranded polynucleotides are second double-stranded cDNA molecules. The synthesis of second antisense cDNA strands can be primed using an oligonucleotide-dT primer. The universal primer site can be added to the 3' end of the second antisense cDNA strands by template switching, oligonucleotide-tailing, or ligation. If an antisense primer complex is employed, the RNA promoter sequence is conveniently one that is recognized by a bacteriophage RNA polymerase, such as T7, T3, or SP6 polymerase.

Preferably, the second double-stranded polynucleotides are produced by amplifying the second antisense polynucleotide strands, and the amplification is carried out using a universal primer that hybridizes to the universal primer site as the 5' primer and using the antisense primer or antisense primer complex as the 3' primer. Most preferably, the amplification is performed by enhanced polymerase chain reaction. This reaction produces a pool of double-stranded polynucleotides that is enriched in low-abundance sequences relative to the original polynucleotide sample. If an antisense primer complex is used to produce second double-stranded polynucleotides, these polynucleotides contain an RNA promoter. In this case, the method can optionally include synthesizing antisense RNA molecules from the second double-stranded polynucleotides.

In preferred embodiments of the methods of the invention, the universal primer and/or the antisense primer or antisense primer complex each comprise a restriction site. The methods of the invention can optionally include cloning one or more of the second double-stranded (low-abundance-enriched) polynucleotides into a vector. In particular, such methods allow the construction of a "normalized" cDNA library. This library is superior to normalized libraries produced by other techniques in that the copy numbers of the cDNAs in the library vary by much less than in the original polynucleotide sample; e.g., highly representative cDNA libraries can be produced in which cDNA copy numbers vary by no more than an order of magnitude. In a preferred variation of this embodiment, the cloned double-stranded polynucleotide encodes a polypeptide, and the vector is an expression vector. The methods of the invention can further include introducing the expression vector into a host cell and expressing the protein encoded by the cloned double-stranded polynucleotide.

The double-stranded polynucleotides produced according to the methods of the invention, or a polynucleotide produced directly or indirectly therefrom, can also be used in a hybridization reaction. Such polynucleotides can be labeled with a detectable label and/or attached to a substrate to produce a polynucleotide array. If desired, one or more of the second double-stranded polynucleotides can be amplified. In a preferred embodiment, this amplification is carried out using one or more gene-specific primers. Accordingly, the methods of the invention encompass each of these applications of these polynucleotides.

In an alternative embodiment, the method for preparing a selected polynucleotide pool from a polynucleotide sample is carried out by synthesizing first antisense polynucleotide strands from sense polynucleotides of, or prepared from, the polynucleotide sample and diluting the first antisense polynucleotide strands to substantially eliminate at least some low-abundance first antisense polynucleotide strands. First double-stranded polynucleotides are then produced from the remaining first antisense polynucleotide strands. These first double-stranded polynucleotides are enriched in high-abundance polynucleotide sequences relative to the polynucleotide sample. They are used to produce second antisense polynucleotide strands, which are then contacted with sense polynucleotide strands of, or prepared from, the polynucleotide sample under hybridization conditions. The resulting hybridization mixture includes unhybridized sense polynucleotide strands that are enriched in low-abundance polynucleotide sequences relative to the polynucleotide sample. Third antisense polynucleotide strands are synthesized from the unhybridized sense polynucleotide strands, and second double-stranded polynucleotides are produced from the third antisense polynucleotide strands. These second double-stranded polynucleotides make up a selected polynucleotide pool that is enriched in low-abundance polynucleotide sequences.

Another aspect of the invention is a plurality of polynucleotides prepared from a polynucleotide sample, wherein the plurality of polynucleotides includes at least $10^3$ different polynucleotides and is either substantially enriched in high-abundance polynucleotide sequences relative to the polynucleotide sample or substantially enriched in low-abundance polynucleotide sequences relative to the polynucleotide sample. Each of the polynucleotides in the plurality of polynucleotides preferably includes a RNA promoter sequence and a universal primer site. In preferred embodiments, these polynucleotides are double-stranded cDNA or antisense RNA.

The invention also provides kits useful for performing the methods of the invention and/or using the plurality of polynucleotides of the invention. A first kit includes: an antisense primer complex including an antisense primer operably linked to an RNA promoter sequence, wherein the RNA promoter sequence is 5' of the antisense primer; a sense primer; and instructions for performing at least one of the above-described methods of the invention. A second kit includes: a plurality of polynucleotides of the invention; an antisense primer complex comprising a antisense primer operably linked to an RNA promoter sequence, wherein the RNA promoter sequence is 5' of the antisense primer; and a sense primer. A third kit includes: a plurality of polynucleotides of the invention, and an RNA polymerase capable of transcribing antisense RNA from the plurality of polynucleotides.

DETAILED DESCRIPTION

The invention is based on novel methods for generating pools of polynucleotides that are enriched in either high- or low-abundance polynucleotides, relative to a polynucleotide sample from which they were derived. In particular, high-abundance polynucleotides are selected by exploiting the loss of low-abundance polynucleotides that occurs upon dilution. Subtractive hybridization between a high-abundance polynucleotide-enriched pool and sample polynucleotides allows the selection of low-abundance polynucleotides in the sample. The methods described herein can be used to replicate a broad range of polynucleotides without prior cloning into vectors and without sequence information. If desired, pools of polynucleotides that represent full-length mRNA transcripts can be produced.

Polynucleotide pools produced according to these methods are useful in a wide variety of applications, such as cloning, expression, and hybridization studies. Pools enriched in low-abundance polynucleotides are particularly useful in studies aimed at identifying important regulatory proteins, since the polynucleotides encoding such proteins tend to be lost using conventional techniques.

I. Definitions

The term "polynucleotide" refers to a deoxyribonucleotide or ribonucleotide polymer, and unless otherwise limited, includes known analogs of natural nucleotides that can function in a similar manner to naturally occurring nucleotides.

The term "polynucleotide" refers any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA.

The term "polynucleotide" encompasses double-stranded polynucleotides, as well as single-stranded molecules. Double-stranded polynucleotides that encode a protein contain a "sense" polynucleotide strand hydrogen-bonded to an "antisense" polynucleotide strand. The sense polynucleotide strand is the strand whose nucleotide sequence, when translated, provides the amino acid sequence of the encoded protein. The term "sense polynucleotide strand" refers, for example, to the sense strands of double-stranded DNA molecules, as well as to mRNA. The antisense polynucleotide strand is complementary to the sense polynucleotide strand. Examples of antisense polynucleotide strands include the antisense strands of double-stranded DNA molecules (e.g., antisense cDNA strands) and antisense RNA molecules. In double-stranded polynucleotides, the polynucleotide strands need not be coextensive (i.e, a double-stranded polynucleotide need not be double-stranded along the entire length of both strands).

As used herein, the term "complementary" refers to the capacity for precise pairing between two nucleotides. If a nucleotide at a given position of a polynucleotide is capable of hydrogen bonding with a nucleotide of another polynucleotide, then the oligonucleotide and the polynucleotide are considered to be complementary to one another at that position. The term "substantially complementary" describes sequences that are sufficiently complementary to one another to allow for specific hybridization under appropriately stringent hybridization conditions.

The phrase "stringent hybridization conditions" generally refers to a temperature about 5° C. lower than the melting temperature ($T_m$) for a specific sequence at a defined ionic strength and pH. Exemplary stringent conditions suitable for achieving specific hybridization of most sequences are a temperature of at least about 60° C. and a salt concentration of about 0.2 molar at pH7.

"Specific hybridization" refers to the binding of a polynucleotide to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

As used with reference to polynucleotide strands, the term "unhybridized" refers to a polynucleotide that remains single-stranded after a hybridization reaction has been carried out under conditions where at least some polynucleotide strands hybridize to form double-stranded polynucleotides.

The term "oligonucleotide" is used to refer to a polynucleotide that is relatively short, generally shorter than 200 nucleotides, more particularly, shorter than 100 nucleotides, most particularly, shorter than 50 nucleotides. Typically, oligonucleotides are single-stranded DNA molecules.

As used herein, the term "selected polynucleotide pool" is used to describe a collection of polynucleotides that represents a subset of the polynucleotides present in a polynucleotide sample used to produce the selected polynucleotide pool.

The term "primer" refers to an oligonucleotide that is capable of hybridizing (also termed "annealing") with a polynucleotide and serving as an initiation site for nucleotide (RNA or DNA) polymerization.

An "antisense primer" is a primer that hybridizes with a nucleotide sequence present in a sense polynucleotide and that can serve as an initiation site for synthesis of an antisense polynucleotide.

A "sense primer" is a primer that hybridizes with a nucleotide sequence present in an antisense polynucleotide and that can serve as an initiation site for synthesis of a sense polynucleotide. As used herein, a sense primer has a sequence that enables it to be used with an antisense primer or antisense primer complex to amplify one or more target polynucleotide sequences.

A "universal primer" is one that hybridizes with a nucleotide sequence present in substantially all polynucleotides intended to serve as the template molecules for nucleotide polymerization.

A "gene-specific primer" is one that hybridizes with a nucleotide sequence present in or flanking a unique expressed sequence, allowing amplification of the unique expressed sequence, or a portion thereof, without substantial amplification of other sequences.

The term "primer site" refers to a region of a polynucleotide that is capable of hybridizing with a primer and serving as an initiation site for nucleotide (RNA or DNA) polymerization.

A "universal primer site" is primer site present in substantially all polynucleotides intended to serve as the template molecules for nucleotide polymerization.

The term "antisense primer complex" is used herein to denote an antisense primer operably linked to an oligonucleotide including an "RNA promoter sequence." The latter sequence is one that provides a promoter in the correct orientation to serve as an initiation site for RNA polymerization.

As used herein, the term "operably linked" refers to a functional linkage between a control sequence (typically a promoter) and the linked sequence. For example, a promoter is operably linked to a sequence if the promoter can initiate transcription of the linked sequence.

The term "abundance" is used to describe the number of copies of a polynucleotide in a polynucleotide sample. A polynucleotide present in a sample at greater than the median number of copies for a polynucleotide of the sample is said to be a "high-abundance polynucleotide." A polynucleotide present in a sample at less than the median number of copies is said to be a "low-abundance polynucleotide." The absolute number of copies of high- or low-abundance sequences varies, depending on the polynucleotide sample. In an mRNA sample, high-abundance sequences include mRNAs transcribed from so-called "housekeeping genes," whereas low-abundance sequences include those encoding regulatory proteins, such as hormones, receptors, or other signaling molecules. Low-abundance mRNAs that can be selected for according to the methods of the invention typically account for less than about 1%, less than about 0.1%, less than 0.01%, or less than about 0.001% of the mRNA present in a cell. The methods of the invention can also be used to select the rarest of mRNAs, which account for on the order of only 0.0000001% of the mRNA present in a cell. mRNA frequencies are typically estimated by screening a cDNA library with a probe that specifically hybridizes to an mRNA of interest. The number of positive clones divided by the total number of clones in the in the library, multiplied by 100%, gives the representation of the sequence in the library, which provides an estimate of mRNA frequency in the cells from which the library was produced.

A pool of polynucleotides is said to be "enriched" in polynucleotides of a given type relative to a polynucleotide sample when such polynucleotides are present in a higher concentration in the pool than in the sample. Low-abundance polynucleotides are said to be "substantially eliminated" if the concentration of such polynucleotides in a pool of polynucleotides is sufficiently reduced that the pool of polynucleotides can be used for applications wherein the presence of low-abundance polynucleotides is undesirable.

The phrase "polynucleotides of a polynucleotide sample" refers to the sample polynucleotides. The phrase "polynucleotides prepared from a polynucleotide sample" refers to polynucleotides produced from sample polynucleotides by RNA or DNA polymerization (e.g., reverse transcription, amplification, synthesis of antisense RNA, etc.) Polynucleotides are "produced directly" from sample polynucleotides when the sample polynucleotides serve as templates for RNA or DNA polymerization. Polynucleotides are "produced indirectly" from sample polynucleotides when more than one polymerization step is employed. Polynucleotides of, or prepared from, a sample are referred to herein as "starting polynucleotides."

As used herein, the term "enhanced polymerase chain reaction" or "enhanced PCR" refers to a polymerase chain reaction capable of amplifying polynucleotide sequences of at least 10 kilobases (kb) in length.

The term "vector" is used herein to describe a DNA construct containing a polynucleotide. Such a vector can be propagated stably or transiently in a host cell. The vector can, for example, be a plasmid, a viral vector, or simply a potential genomic insert. Once introduced into a suitable host, the vector may replicate and function independently of the host genome, or may, in some instances, integrate into the host genome.

"Expression vector" refers to a DNA construct containing a polynucleotide molecule that is operably linked to a control sequence capable of effecting the expression of the polynucleotide in a suitable host. Exemplary control sequences include a promoter to effect transcription, an optional operator sequence to control transcription, a sequence encoding suitable mRNA ribosome binding sites, and sequences that control termination of transcription and translation.

The term "host cell" refers to a cell capable of maintaining a vector either transiently or stably. Host cells of the invention include, but are not limited to, bacterial cells, yeast cells, insect cells, plant cells and mammalian cells. Other host cells known in the art, or which become known, are also suitable for use in the invention.

The term "array" refers to a collection of elements, wherein each element is uniquely identifiable. For example, the term can refer to a substrate bearing an arrangement of elements, such that each element has a physical location on the surface of the substrate that is distinct from the location of every other element. In such an array, each element can be identifiable simply by virtue of its location. Typical arrays of this type include elements arranged linearly or in a two-dimensional matrix, although the term "array" encompasses any configuration of elements and includes elements arranged on non-planar, as well as planar, surfaces. Non-planar arrays can be made, for example, by arranging beads, pins, or fibers to form an array. The term "array" also encompasses collections of elements that do not have a fixed relationship to one another. For example, a collection of beads in which each bead has an identifying characteristic can constitute an array.

The elements of an array are termed "target elements."

As used herein with reference to target elements, the term "distinct location" means that each element is physically separated from every other target element such that a signal (e.g., a fluorescent signal) from a labeled molecule bound to target element can be uniquely attributed to binding at that target element.

A "microarray" is an array in which the density of the target elements on a substrate surface is at least about $100/cm^2$.

As used herein, "substantially enriched" means an enrichment of about 100-fold; i.e., a selected polynucleotide pool is substantially enriched in high- or low-abundance sequences if the concentrations of each of a plurality of such sequences is at least about 100-fold higher in the selected polynucleotide pool relative to the original polynucleotide sample from which the pool was derived. For this purpose, enrichment can be estimated by hybridizing a labeled probe to the polynucleotide sample and to the selected polynucleotide pool and comparing the hybridization signal observed for each. For example, a Northern blot can be prepared from the polynucleotide sample and the selected polynucleotide pool and hybridized with a radioactively labeled probe, followed by autoradiography. The autoradiograph can be scanned using laser densitometry to quantitate the hybridization signal. Other techniques for determining the intensity of a hybridization signal, e.g., array-based methods, are well known and can be employed to assess enrichment of polynucleotide sequences in the present invention. "Fold enrichment" is calculated by dividing the hybridization signal observed for the selected polynucleotide pool by the hybridization signal observed for the polynucleotide sample.

II. Methods for Preparing Selected Polynucleotide Pools

The invention provides methods for selecting polynucleotide pools from a polynucleotide sample. One method exploits on the loss of low-abundance sequences during dilution to produce a polynucleotide pool that is enriched in high-abundance polynucleotide sequences relative to the polynucleotide sample. A second method begins with a high-abundance polynucleotide pool produced by the dilution method of the invention or otherwise. This method relies on subtractive hybridization with the high-abundance polynucleotide pool to produce a low-abundance-enriched polynucleotide pool.

A. Preparation of a Polynucleotide Pool that is Enriched in High-Abundance Polynucleotide Sequences 1. Synthesis of Antisense Polynucleotide Strands from a Polynucleotide Sample To prepare a polynucleotide pool that is enriched in high-abundance polynucleotide sequences, antisense polynucleotide strands are first synthesized from sense polynucleotide strands of a polynucleotide sample or sense polynucleotide strands prepared from a polynucleotide sample.

Essentially any polynucleotides can be used as the starting polynucleotides for the methods of the present invention, provided they each contain nucleotide sequences substantially complementary to an antisense primer. This antisense primer site can be located at the 3' end of the sense polynucleotide strands (e.g., the poly-A tail of mRNA molecules), which produces full-length antisense polynucleotide strands. Alternatively, the antisense primer site can be located so that antisense polynucleotide strands are synthesized for only a portion of the sense polynucleotide strands.

The starting polynucleotides can be obtained from any source, such as for example, from polynucleotide libraries, including cDNA, cosmid, YAC, or BAC libraries, and the like. DNA or RNA useful in the invention can be extracted and/or amplified from any source, including bacteria, yeast, viruses, organelles, as well higher organisms such as plants or animals, with mammals being preferred, and humans being most preferred. Starting polynucleotides can also be extracted or amplified from cells, blood, or tissue samples by a variety of standard techniques. The starting polynucleotides need not be present initially in a pure form; they can be a minor fraction of a complex mixture, provided that other components in the mixture do not substantially interfere with the synthesis of the antisense polynucleotide strands.

In preferred embodiments, synthesis of antisense polynucleotide strands is primed using an antisense primer complex. As stated above, the antisense primer complex has two components: (1) an antisense primer and (2) a specifically oriented RNA polymerase promoter sequence. The antisense primer complex can also contain a sequence that is a restriction endonuclease site (restriction site), which can facilitate cloning of polynucleotide pools produced according to the methods of the invention.

The antisense primer is capable of acting as a point of initiation of polynucleotide synthesis, typically DNA replication, when placed under conditions suitable for primer extension, i.e., in the presence of appropriate nucleotides and a replicating agent (e.g., a DNA polymerase) under suitable reaction conditions, which are well known in the art. The primer is preferably a single-stranded oligonucleotide, most preferably and oligodeoxynucleotide. The primer must be sufficiently long and have a sequence that allows formation of a sufficiently stable duplex with the starting polynucleotides to permit the synthesis of extension products in the presence of the replicating agent. The exact lengths of the primers and the quantities used will depend on many factors, including hybridization temperature, ionic conditions, degree of homology, and other factors familiar to those of skilled in the art. A primer designed to hybridize to a specific sequence motif typically contains between about 10 and about 50 nucleotides, and preferably between about 15 and about 25 or more nucleotides, although the primer can contain fewer nucleotides, depending, e.g., on the sequence motif. For other applications, the oligonucleotide primer is typically, but not necessarily, shorter, e.g., about 7 to about 15 nucleotides. As those of skill in the art readily appreciate, such short primer molecules generally require lower hybridization temperatures to form sufficiently stable hybrid complexes with template polynucleotides.

Antisense primers can be produced by any available method. Oligonucleotide primers are conveniently synthesized, for example, by the well known phosphotriester and phosphodiester methods, especially the automated versions thereof. A standard automated method uses diethylphosphoramidites as starting materials, which can be purchased commericially or synthesized as described by Beaucage et al., Tetrahedron Letters 22: 1859–1962 (1981) or in U.S. Pat. No. 4,458,066. It is also possible to use primers that have been isolated from a biological source (e.g., via a restriction endonuclease digest or amplification).

Antisense primers useful in the methods of the invention are substantially complementary to the antisense primer sites in the starting polynucleotides. Therefore, a given antisense primer sequence need not be the exact complement of the antisense primer site to which it hybridizes. Non-complementary bases or longer sequences can be present the primer, provided that the primer sequence has sufficient complementarity with the sequence of the antisense primer site to permit hybridization and polynucleotide extension.

The second component of the antisense primer complex is an RNA promoter sequence. Such sequences are capable of binding an RNA polymerase and contain a transcriptional start site. The RNA promoter sequence employed in the antisense primer complex may be single stranded or double stranded. The promotor sequence usually includes between about 15 and about 250 nucleotides, preferably between about 25 and about 60 nucleotides, from a naturally occurring RNA polymerase promoter, a consensus promoter sequence (Alberts et al., in Molecular Biology of the Cell, 2d Ed., Garland, N.Y. (1989), or modified versions thereof.

A wide variety of promoters and polymerases showing specificity for their cognate promoter are known. In general, prokaryotic promoters are preferred over eukaryotic promoters, and phage or virus promoters most preferred. Particularly preferred are the T3, T7, and SP6 phage promoter/polymerase systems. Probably the best studied is E.coli phage T7. T7 makes an entirely new polymerase that is highly specific for the 17 late T7 promoters. Rather than having two separate highly conserved regions like E.coli promoters, the late T7 promoters have a single highly conserved sequence from −17 to +6 relative to the RNA start site. The Salmonella phage SP6 is very similar to T7. Although most RNA polymerases recognize double-stranded promoters, E.coli phage N4 makes an RNA polymerase that recognizes early N4 promoters on native single stranded N4 DNA. A detailed description of promoters and RNA synthesis upon DNA templates is found in Watson et al., Molecular Biology of The Gene, 4th Ed., Chapters 13–15, Benjamin/Cummings Publishing Co., Menlo Park, Calif. A preferred promoter sequence is the sequence from the T7 phage that corresponds to its RNA polymerase binding site (5'-AAT TcT AAT ACG ACT CAC TAT AGG G-3'; SEQ ID NO:1).

The RNA promoter sequence is linked to the antisense primer to facilitate transcription in the presence of ribonucleotides and an RNA polymerase under suitable conditions. The primer and promoter components are linked with the RNA promoter upstream (5') of the antisense primer in an orientation that permits transcription of a polynucleotide strand that is complementary to the primer, i.e., such that antisense RNA transcription (described in detail below) will generally be in the same direction as the primer extension. Any type of linkage that meets this criterion can be employed, however nucleotide linkages are preferred. A linker oligonucleotide between the components, if present, typically includes between about 5 and about 20 bases, but may be smaller or larger as desired.

In a preferred embodiment, the sample is an RNA sample. To produce a selected polynucleotide pool from total RNA, a plurality of primer complexes containing antisense primers of random sequence (i.e., "random primers") can be employed. To produce a selected polynucleotide pool from the mRNA present in a sample, the antisense primer can include a polythymidylate (also termed "oligonucleotide-dT" or "oligo-dT") sequence (e.g., about 5 to about 50, preferably about 5 to about 20, more preferably about 10 to about 15 T residues, which will hybridize with the poly(A) tail present at the 3' terminus of each mRNA present in the sample. Preferably, antisense cDNA strands are synthesized from mRNA. If the mRNA is already purified, cDNA synthesis can be primed using random primers or a polythymidylate primer. If cDNA synthesis is carried out using total RNA, a polythymidylate (oligonucleotide-dT) primer is typically employed. Alternatively, if only RNA sharing a common nucleotide sequence motif is to be amplified, then the primer is substantially complementary to this sequence motif.

Once the antisense primer and operably linked promoter region hybridize to the sense polynucleotides in a sample, an antisense polynucleotide strand is synthesized. If the sense polynucleotides are mRNA, a first strand of cDNA is conveniently produced through the process of reverse transcription, wherein DNA is made from RNA, utilizing reverse transcriptase according to standard techniques. This enzyme, present in all retroviruses (e.g., avian myeloblastoma virus), adds deoxyribonucleotides to the 3' terminus of the primer (Varmus, Science 240: 1427–1435 (1988)).

2. Addition of a Universal Primer Site

After synthesis of antisense polynucleotide strands from the sense polynucleotide strands of, or prepared from, the polynucleotide sample, a universal primer site is preferably added to the 3' ends of the antisense polynucleotide strands. The universal primer site is present in an oligonucleotide that is ligated or otherwise linked the antisense polynucleotide strands. The oligonucleotide can be an oligodeoxynucleotide, an oligoribodeoxynucleotide, or a hybrid molecule containing deoxynucleotides and ribodeoxynucleotides. The universal primer site should have a length and sequence suitable for hybridizing to a universal primer. In preferred embodiments, the universal primer site serves as an "anchor" for an amplification reaction, which is conveniently carried our using the polymerase chain reaction ("PCR"). The universal primer site can also include a restriction site, if desired, to facilitate cloning of polynucleotide pools of the invention. The considerations for selecting a suitable universal primer site sequence are well-known in the art. The usual and preferred lengths for such sequences are the same as those given above for the the antisense primer.

The universal primer site can be added to the antisense polynucleotide strands by any convenient method. Examples of suitable methods include "template switching," "oligonucleotide-tailing," and ligation.

Template switching is described in U.S. Pat. No. 5,962,727 (issued Oct. 5, 1999 to Chenchik, et al.). This technique is typically used when antisense cDNA strands are being synthesized from an mRNA sample and offers the advantage that the strand synthesis and addition of the universal primer site can be carried out in a single reaction mixture. Briefly, a template-switching oligonucleotide is included during reverse transcription, which produces an mRNA-antisense cDNA hybrid. The template-switching oligonucleotide hybridizes to the CAP site at the 5' end of mRNA strand and serves as a short, extended template for CAP-dependent extension of the 3' end of the antisense cDNA strand. Template-switching oligonucleotides typically require a few ribonucleotides at the 3' end to promote CAP-dependent extension. Thus, template-switching oligonucleotides generally contain between about 1 and about 5 ribonucleotides at their 3' ends.

In oligonucleotide-tailing (also termed "homopolymeric tailing"), deoxynucleotides of a particular type, i.e., dA, dT, dG, or dC, are added to an antisense DNA strand using a terminal transferase. This reaction produces an antisense DNA strand with an oligonucleotide-dA, -dT, -dG, or -dC tail that can serve as a universal primer site for an oligonucleotide-dT, -dA, -dC, or -dG primer, respectively.

The universal primer site can also be added by ligating an oligonucleotide to the 3' end of the antisense polynucleotide strand, as described, for example in Akowitz, Gene 81:295–306 (1989). A DNA ligase is employed to ligate the oligonucleotide to a DNA strand, and an RNA ligase is employed to ligate the oligonucleotide to an RNA strand. Where the sense polynucleotides are RNA, an RNA ligase can be used to join an oligonucleotide to the 5' ends of the RNA molecules, followed by reverse transcription to produce antisense cDNA molecules that incorporate a universal primer site at their 3' ends. See, e.g., Fromont-Racine, Nucl. Acids. Res. 21:1683–1684 (1993); Suzuki, Gene 100:149–156 (1997). In this embodiment, an oligodeoxynucleotide or an oligoribodeoxynucleotide can be employed.

3. Dilution of Antisense Polynucleotide Strands

After production of antisense polynucleotide strands, preferably containing universal primer sites, the reaction mixture is diluted to substantially eliminate low-abundance antisense polynucleotide strands. Serial dilution is typically employed for this purpose, and the degree of dilution depends upon desired abundance threshold. Minimal dilution removes the rarest polynucleotide stands in the mixture, whereas greater dilution removes polynucleotide strands that are present in higher copy number. Dilutions useful for standard applications of the method range from $10^{-1}$, $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, and $10^{-12}$, although higher or lower dilutions may be desirable in specific applications. A serial dilution is made by removing an aliquot of the reaction mixture and transferring the aliquot to a volume of an aqueous solution that provides the desired degree of dilution. If desired, multiple transfers may be used to achieve a stepwise dilution that yields the desired degree of dilution. The aqueous solution used for dilution is preferably one that is compatible the enzymes used in the next step of the method to produce double-stranded polynucleotides from the antisense polynucleotide strands present after dilution.

4. Production of First Double-Stranded Polynucleotides from Remaining Antisense Polynucleotide Strands Double-stranded polynucleotides can be produced from the antisense polynucleotide strands remaining after dilution by any of a number of available methods. Second-stranded cDNA, for example, can be synthesized using RNase H and E. coli DNA polymerase, optionally including DNA ligase. RNase assists in breaking the RNA/first-strand cDNA hybrid, and DNA polymerase synthesizes a complementary DNA strand using the first-strand cDNA as template. The second strand is generated as deoxynucleotides are added to the 3' terminus of the growing strand. As the growing strand reaches the 5' terminus of the first strand DNA, the complementary promoter region of the first strand is copied into the double stranded promoter sequence in the desired orientation.

In a preferred embodiment, double-stranded polynucleotides are produced by amplification. If the antisense polynucleotide strands are cDNA molecules in a RNA/first-strand cDNA hybrid, the RNA sequences are preferably removed prior to amplification by any suitable technique, such as, for example, treatment with sodium hydroxide. Amplification is preferably carried out by PCR, and more preferably by enhanced PCR, both of which are well-known to those of skilled in the art. PCR is described in U.S. Pat. Nos. 4,683,202, 4,683,195, 4,800,159, and 4,965,188, as well as in Saiki, Science 230:1350 (1985). PCR entails hybridizing two primers to substantially complementary sequences that flank a target sequence in a polynucleotide. A repetitive series of reaction steps involving template denaturation, primer annealing, and extension of the annealed primers by a DNA polymerase results in the geometric accumulation of a the target sequence whose termini are defined by the 5' ends of the primers. As denaturation is typically carried out at temperatures that denature most DNA polymerases (e.g., about 93° C.–95° C.), a thermostable polymerase, such as those derived from Thermus thermophilus, Thermus aquaticus (Taq), or Thermus flavus, is typically used for extension to avoid the need to add additional polymerase for each extension cycle.

In a preferred embodiment, antisense polynucleotide strands are amplified using enhanced PCR. Enhanced PCR can be carried out as described, for example, in U.S. Pat. No. 5,436,149 (issued Jul. 25, 1995 to Barnes et al.), which discloses the use of a polymerase combination including a variant of Taq or Thermus flavus DNA polymerase lacking 3'-exonuclease activity and a lesser amount of a thermostable DNA polymerase having such activity. A similar polymerase combination that can also be used in the method is described in U.S. Pat. No. 5,512,462 (issued Apr. 30, 1996 to Cheng). The considerations affecting the selection of PCR primers and amplification conditions are well known, and those of skill in the art can readily determine primers and conditions suitable for a particular application of the method of the invention.

PCR amplification of antisense polynucleotides that have a 3' universal primer site is conveniently accomplished, for example, by using a universal primer that hybridizes to the universal primer site as the 5' primer and using the antisense primer complex as the 3' primer. Thus, such primers are preferably selected to serve as anchors for efficient and sufficiently specific PCR amplification.

The pool of polynucleotides produced from antisense polynucleotide strands is enriched in high-abundance polynucleotide sequences with respect to the starting polynucleotide sample and can be used, for example, in a subtractive hybridization method of the invention to produce a selected polynucleotide pool that is enriched in low-abundance polynucleotide sequences relative to the starting polynucleotide sample, as described in greater detail below. For clarity, the high-abundance-enriched polynucleotides are termed the "first double-stranded polynucleotides," and the low-abundance-enriched polynucleotides discussed below are termed the "second double-stranded polynucleotides."

Where the polynucleotide sample is an mRNA sample, the first double-stranded polynucleotides are referred to as "cDNA" molecules. In preferred embodiments, the first double-stranded polynucleotides retain the universal primer site at the 5' end (relative to the sense strand) and a functional RNA polymerase at the 3' end (relative to the sense strand).

5. Synthesis of Antisense RNA from First Double-Stranded Polynucleotides

Anti-sense RNA (aRNA) can be synthesized from first double-stranded polynucleotides containing an RNA promoter by contacting the polynucleotides with an RNA polymerase capable of binding to the RNA promoter region under conditions suitable for RNA synthesis. The sense strand is transcribed into aRNA. Amplification occurs because the polymerase repeatedly recycles on the template (i.e., reinitiates transcription from the promoter region). This technique permits the replication of a broad range of polynucleotides without the need for cloning into vectors. In addition, recycling of the polymerase on the same template avoids propagation of errors.

The RNA polymerase used for the transcription must be capable of operably binding to the particular promoter region employed in the antisense primer complex described above. Substantially any polymerase/promoter combination can be used; however, bacteriophage RNA polymerases, in particular from T3, T7, and SP6 phages, are preferred. The most preferred polymerase is T7 RNA polymerase. The extremely high degree of specificity shown by T7 RNA polymerase for its promoter site (Chamberlin et al., in The Enzymes, ed. P. Boyer (Academic Press, New York) pp. 87–108 (1982)) has previously made this enzyme a useful reagent in a variety of recombinant DNA techniques, including in vitro RNA synthesis from plasmids containing the promoter site for use as probes (Melton et al., Nucl. Acids Res., 12: 7035–7056 (1984)), for in vitro translation studies (Krieg et al., Nuc. Acids Res. 12: 7057–7070 (1984)), and for use in producing synthetic oligoribonucleotides (Milligan et al., Nuc. Acids Res. 15: 8783–8798 (1987)). The lack of efficient termination signals for T7 polymerase also enables this enzyme to transcribe almost any DNA sequence (see, Rosenberg et al., Gene 56: 125–135 (1987)). Finally, T7 polymerase is available from a number of commercial sources, such as Promega Biotech, Madison, Wis., and in a concentrated form (1000 units/$\mu$l) from Epicenter Technologies, Madison, Wis. $E.coli$ RNA polymerase can also be employed with an appropriate $E.coli$ RNA polymerase promoter region.

The transcription reaction mixture includes the necessary nucleotide triphosphates, which may be modified, depending on the ultimate use of the aRNA. For example, if the aRNA is intended for use as a nucleic hybridization probe, one or more of the nucleotides may be labeled, as described in greater detail below.

B. Preparation of a Polynucleotide Pool that is Enriched in Low-Abundance Polynucleotide Sequences 1. Subtractive Hybridization of a Polynucleotide Sample with Antisense Polynucleotides that are Enriched in High-Abundance Polynucleotide Sequences In a preferred embodiment, the aRNA of the invention is used in a subtractive hybridization method. Because aRNA is anti-sense with respect to the sense polynucleotide strands of the original sample, aRNA produced as described above can be hybridized with sense polynucleotides of, or prepared from, the polynucleotide sample. This hybridization reaction produces double-stranded polynucleotides and unhybridized sense polynucleotides. Because the aRNA is enriched in high-abundance sequences, the high-abundance sequences become double-stranded, and the unhybridized sense polynucleotides are enriched in low-abundance sequences relative to the polynucleotide sample.

Antisense polynucleotide strands for use in the subtractive hybridization method of the invention can also be prepared from a polynucleotide sample by other means known to those of skill in the art. For example, antisense polynucleotide strands enriched in high-abundance polynucleotide sequences, relative to the polynucleotide sample from which they were derived, can be produced by taking advantage of the differences in reassociation kinetics between high-abundance and low-abundance sequences. If polynucleotides are denatured and allowed to reassociate, the sequences present in the sample at a higher copy number will reassociate before the lower-copy number sequences. Thus, sequences that become double-stranded relatively quickly (e.g., Cot=5.5 or less, where Co is moles of nucleotide/liter and t is time in seconds) represent high-abundance polynucleotide sequences. These double-stranded sequences can be recovered from the reassociation mixture and used to produce antisense polynucleotides for use in the subtractive hybridization method of the invention.

The antisense polynucleotide strands and the sense polynucleotide strands used in the subtractive hybridization are preferably derived from the same polynucleotide sample. However, the method of the invention also encompasses the subtractive hybridization of antisense polynucleotide strands derived from one polynucleotide sample and sense polynucleotide strands of, or prepared from, a different polynucleotide sample. In this case, subtractive hybridization would remove low-abundance sequences shared by the two samples.

For subtractive hybridization, the antisense polynucleotide strands are contacted with the sense polynucleotide strands under conditions wherein at least some of the polynucleotides hybridize to one another. In a preferred embodiment, the sense polynucleotide strands are mRNA molecules. In a particularly preferred variation of this embodiment, the antisense polynucleotide strands are aRNA.

The antisense polynucleotide strands are usually added to the hybridization reaction in excess to drive hybridization (this component of the reaction is thus sometimes termed the "driver"), although this is not a requirement of the method. For most applications, the molar ratio of antisense polynucleotide to other polynucleotides in the reaction mixture is between about 1:1 and about 800:1, preferably between about 1:1 and about 200:1, and more preferably between about 1:1 and about 100:1, although other ratios are possible.

The hybridization reaction is carried out at high temperature, usually between about 60–70° C., to achieve relatively specific hybridization. In addition, buffers and salt concentrations used can be adjusted to achieve the necessary stringency using techniques known to those of skill in the art. Typically, fairly high stringencies are preferred. Accepted methods for conducting hybridization assays are known, and general overviews of the technology are found in: Nucleic Acid.Hybridization: A Practical Approach, Ed. Hames, B. D. and Higgins, S. J., IRL Press, 1985; Hybridization of Nucleic Acids Immobilized on Solid Supports, Meinkoth, J. and Wahl, G.; Analytical Biochemistry, 238:267–284, 1984 and Innis, et al., PCR Protocols, supra. Subtractive hybridization techniques are also specifically described in U.S. Pat. No. 5,589,339 (issued Dec., 31, 1996 to Hampson et al.), U.S. Pat. No. 5,935,788 (issued Aug. 10, 1999 to Burmer et al.), and U.S. Pat. No. 5,958,738 (issued Sep. 28, 1999 to Lindemann et al.).

2. Synthesis of Antisense Polynucleotide Strands from Unhybridized Sense Polynucleotide Strands The unhybridized sense polynucleotides from the subtractive hybridization reaction can then, if desired, be used as templates for the synthesis of another set of antisense polynucleotide strands. Although any standard technique can be employed for this purpose, in preferred embodiments, this second set of antisense polynucleotide strands is synthesized using an antisense primer or an antisense primer complex, as described above. If an antisense primer complex is employed, the antisense polynucleotide strands contain a primer site and an RNA promoter sequence at the 5' end. Thus, an antisense primer complex is preferably employed if it is desirable to produce a pool of selected polynucleotides that each include an RNA promoter to facilitate the synthesis of antisense RNA from the selected polynucleotides. If the primer site and/or the RNA promoter sequence are to be used to initiate nucleotide synthesis in reaction mixtures that may contain undesired polynucleotides also having primer sites and/or promoter sequences, the primer sites and/or promoter sequences are preferably sufficiently different to allow specific nucleotide synthesis from the desired polynucleotides. Regardless of the method employed, the antisense polynucleotide strands produced from the unhybridized sense polynucleotides are enriched in low-abundance sequences relative to the polynucleotide sample.

Where the unhybridized sense polynucleotide are mRNA molecules, the mRNA is conveniently reverse transcribed to produce antisense cDNA strands as the low-abundance antisense polynucleotide strands.

3. Addition of a Universal Primer Site

In preferred embodiments of the invention, a universal primer site is added to the 3' end of low-abundance antisense polynucleotide strands as described above to facilitate simultaneous synthesis and amplification of double-stranded low-abundance polynucleotides. The universal primer site is preferably added by template switching, oligonucleotide-tailing, or ligation. If the primer site is to be used to initiate nucleotide synthesis in reaction mixtures that may contain undesired polynucleotides also having a universal primer site, the primer site incorporated into the low-abundance antisense polynucleotide strands is preferably sufficiently different to allow specific nucleotide synthesis from the desired polynucleotides.

4. Production of Double-Stranded Polynucleotides from Antisense Polynucleotide Strands Double-stranded polynucleotides can be produced from low-abundance antisense polynucleotide strands as described above. If a 3' universal primer site has been added to the antisense polynucleotide stands, the polynucleotide strands are preferably amplified using PCR, and more preferably using enhanced PCR. This amplification is conveniently carried out using a universal primer that hybridizes to the universal primer site as the 5' primer and using the antisense primer or antisense primer complex as the 3' primer. These primers can include a restriction site, if desired, to facilitate cloning of polynucleotide pools of the invention. The resultant pool of polynucleotides is enriched in low-abundance polynucleotide sequences with respect to the starting polynucleotide sample.

If the low-abundance antisense polynucleotide strands are cDNA molecules in a RNA/first-strand cDNA hybrid, the RNA sequences are preferably removed prior to amplification by any suitable technique, such as, for example, treatment with sodium hydroxide. Amplification then produces double-stranded cDNA molecules.

III. Selected Polynucleotide Pools

The invention also provides selected polynucleotide pools containing a plurality of polynucleotides prepared from a polynucleotide sample that is substantially enriched in high- or low-abundance polynucleotide sequences relative to the polynucleotide sample. In preferred embodiments, the high- or low-abundance polynucleotide sequences are about $10^3$-, about $10^4$-, about $10^5$-, about $10^6$-, or about $10^7$-fold enriched, relative to the polynucleotide nucleotide sample. Preferably, the plurality of polynucleotides includes at least about $10^2$, at least about $10^3$, at least about $10^4$, at least about $10^5$, at least about $10^6$, or at least about $10^7$ different polynucleotide sequences.

In preferred embodiments, the polynucleotides each include an RNA promoter sequence and a universal primer site. The polynucleotides can be any form of DNA or RNA and can be single- or double-stranded. Preferably, the polynucleotides are cDNA or aRNA.

The polynucleotide pools of the invention are useful in a wide variety of applications. Although the following description discusses uses of the pools, those of skill in the art understand that an individual polynucleotide can be selected from a polynucleotide pool and used essentially as described for the pools. Polynucleotide pools selected according to the above methods can be cloned into vectors using standard cloning techniques to produce polynucleotide libraries. Such libraries can facilitate studies of gene expression in essentially any cell or cell population. The subject cells may be obtained from blood (e.g., white cells, such as T or B cells) or other tissues, such as brain, spleen, bone, heart, vascular, lung, kidney, liver, pituitary, endocrine glands, lymph nodes, dispersed primary cells, tumor cells, or the like. In the area of neural research, for example, the identification of mRNAs that vary as a function of, e.g., arousal state, behavior, drug treatment, and development has been hindered by both the difficulty of constructing cDNA libraries from small brain nuclei. Use of polynucleotide pools in accordance with the invention to construct cDNA libraries from individual brain nuclei provides for greater representation of low-abundance mRNAs from these tissues compared with their representation in whole brain cDNA libraries and facilitates the cloning of important low-abundance messages.

Vectors suitable for use in cloning typically contain a replication sequence capable of effecting replication of the vector in a suitable host cell (i.e., an origin of replication) as well as sequences encoding a selectable marker, such as an antibiotic resistance gene. Upon introduction of the vector into a suitable host, the vector can replicate and function independently of the host genome or integrate into the host genome. Vector design depends, among other things, on the intended use and host cell for the vector, and the design of a vector of the invention for a particular use and host cell is within the level of skill in the art.

In a preferred embodiment, the polynucleotides of the invention encode polypeptides and are cloned into expression vectors. Expression vectors include one or more control sequences capable of effecting and/or enhancing the expression of an operably linked protein coding sequence. Control sequences that are suitable for expression in prokaryotes, for example, include a promoter sequence, an operator sequence, and a ribosome binding site. Control sequences for expression in eukaryotic cells include a promoter, an enhancer, and a transcription termination sequence (i.e., a polyadenylation signal). An expression vector useful in the methods of the invention can also include other sequences, such as, for example, sequences encoding a signal sequence or an amplifiable gene. A signal sequence directs the secretion of a polypeptide fused thereto from a cell expressing the protein. The inclusion in a vector of a gene complementing an auxotrophic deficiency in the chosen host cell allows for the selection of host cells transformed with the vector.

A vector of the present invention is typically produced by linking desired elements by ligation at convenient restriction sites. Cloning can be simplified if the antisense primer or antisense primer complex and the universal primer site used to generate the polynucleotides of the invention include restriction sites. The inclusion of different restriction sites in the primer or primer complex and the universal primer site facilitates directional cloning. Preferably, the restriction sites used occur infrequently in the polynucleotides of the original sample, to minimize internal cutting of the polynucleotides of the invention. Examples of suitable sites include those recognized by SfiI and NotI.

Vectors containing the cloned polynucleotides can be introduced into host cells. A wide variety of host cells are available for propagation and/or expression of vectors. Examples include prokaryotic cells (such as *E. coli* and strains of Bacillus, Pseudomonas, and other bacteria), yeast or other fungal cells (including *S. cerevesiae* and *P. pastoris*), insect cells, and plant cells, as well as higher eukaryotic cells (such as human embryonic kidney cells and other mammalian cells). Host cells according to the invention include cells in culture and cells present in live organisms, such as transgenic plants or animals.

Vectors can be introduced into host cells by any convenient method, which will vary depending on the vector-host system employed. Generally, a vector is introduced into a host cell by transformation (also known as "transfection") or infection with a virus (e.g., phage) bearing the vector. If the host cell is a prokaryotic cell (or other cell having a cell wall), convenient transformation methods include the calcium treatment method described by Cohen, et al. (1972) Proc. Natl. Acad. Sci., USA, 69:2110–14. If a prokaryotic cell is used as the host and the vector is a phagemid vector, the vector can be introduced into the host cell by infection. Yeast cells can be transformed using polyethylene glycol, for example, as taught by Hinnen (1978) Proc. Natl. Acad. Sci, USA, 75:1929–33. Mammalian cells are conveniently transformed using the calcium phosphate precipitation method described by Graham, et al. (1978) Virology, 52:546 and by Gorman, et al. (1990) DNA and Prot. Eng. Tech., 2:3–10. However, other known methods for introducing DNA into host cells, such as nuclear injection, electroporation, and protoplast fusion also are acceptable for use in the invention.

Host cells transformed with expression vectors can be used to express the polypeptides encoded by the cloned polynucleotides of the invention. Expression entails culturing the host cells under conditions suitable for cell growth and expression and recovering the expressed polypeptides from a cell lysate or, if the polypeptides are secreted, from the culture medium. In particular, the culture medium contains appropriate nutrients and growth factors for the host cell employed. The nutrients and growth factors are, in many cases, well known or can be readily determined empirically by those skilled in the art. Suitable culture conditions for mammalian host cells, for instance, are described in Mammalian Cell Culture (Mather ed., Plenum Press 1984) and in Barnes and Sato (1980) Cell 22:649.

In addition, the culture conditions should allow transcription, translation, and protein transport between cellular compartments. Factors that affect these processes are well-known and include, for example, DNA/RNA copy number; factors that stabilize DNA; nutrients, supplements, and transcriptional inducers or repressors present in the culture medium; temperature, pH and osmolality of the culture; and cell density. The adjustment of these factors to promote expression in a particular vector-host cell system is within the level of skill in the art. Principles and practical techniques for maximizing the productivity of in vitro mammalian cell cultures, for example, can be found in Mammalian Cell Biotechnology: a Practical Approach (Butler ed., IRL Press (1991).

Any of a number of well-known techniques for large- or small-scale production of proteins can be employed in expressing the polypeptides of the invention. These include, but are not limited to, the use of a shaken flask, a fluidized bed bioreactor, a roller bottle culture system, and a stirred tank bioreactor system. Cell culture can be carried out in a batch, fed-batch, or continuous mode.

Methods for recovery of recombinant proteins produced as described above are well-known and vary depending on the expression system employed. A polypeptide including a signal sequence can be recovered from the culture medium or the periplasm. Polypeptides can also be expressed intracellularly and recovered from cell lysates.

The expressed polypeptides can be purified from culture medium or a cell lysate by any method capable of separating the polypeptide from one or more components of the host cell or culture medium. Typically, the polypeptide is separated from host cell and/or culture medium components that would interfere with the intended use of the polypeptide. As a first step, the culture medium or cell lysate is usually centrifuged or filtered to remove cellular debris. The supernatant is then typically concentrated or diluted to a desired volume or diafiltered into a suitable buffer to condition the preparation for further purification.

The polypeptide can then be further purified using well-known techniques. The technique chosen will vary depending on the properties of the expressed polypeptide. If, for example, the polypeptide is expressed as a fusion protein containing an affinity domain, purification typically includes the use of an affinity column containing the cognate binding partner. For instance, polypeptides fused with hexahistidine or similar metal affinity tags can be purified by fractionation on an immobilized metal affinity column.

Polynucleotide pools prepared according to the invention can also be used as templates for cDNA synthesis and/or subjected to amplification to further expand one or more desired sequences. Amplification is preferably carried out by PCR, and more preferably by enhanced PCR. The entire pool can be amplified, preferably using an appropriate antisense primer or antisense primer complex and universal primer, or a subset of the pool can be amplified. Individual sequences of interest can be amplified using at least one, and preferably two, gene-specific primers. Alternatively, aRNA can be synthesized from the polynucleotide pools as described above.

The polynucleotide pools, or polynucleotides (such as aRNA) produced from them, can be used in a hybridization reaction. If desired, the pools or polynucleotides produced therefrom can be labeled with a detectable label. A wide variety of labeling techniques are well known to those skilled in the art and can be used to produce labeled polynucleotides of the invention in accordance with standard procedures (see U.S. Pat. No. 4,755,619). The labeling step can be incorporated into one of the above-described reactions so that the above-described methods produce labeled polynucleotide pools. For example, one or more nucleotide triphosphates can be included in a reaction mixture. Suitable labels are well known and include, for example, a radioactive label, such as $^{32}S$, $^{32}P$, $^{3}H$, and the like, or a non-radioactive label, such a fluorescent label. Labeling may be direct or indirect. In an example of the latter, one or more biotinylated nucleotides is used to synthesize biotinylated polynucleotides (see, Sive and St. John, Nucl. Acids Res. 16: 10937 (1988) and Duguid et al., Proc. Natl. Acad. Sci. USA 85: 5738–5742 (1988)). The biotinylated polynucleotides can then be detected by binding to labeled avidin.

The polynucleotide pools of the invention, or polynucleotides produced therefrom, can, if desired, be attached to one or more substrates to produce a polynucleotide array, which can then be used in a hybridization assay. In a preferred embodiment, each type of polynucleotide constitutes a different target element in the array. Preferably, polynucleotide pools of the invention are used to produce DNA microarrays.

Arrays of polynucleotides of the invention can be produced in accordance with conventional techniques for DNA array fabrication. For example, a sample dispenser mounted on a device that can be precisely positioned can be employed to spot samples onto a substrate. U.S. Pat. No. 5,807,522 (issued Sep. 15, 1998 to Brown and Shalon) describes a device that facilitates mass fabrication of microarrays characterized by a large number of micro-sized assay regions separated by a distance of 50–200 microns or less and a well-defined amount of analyte (typically in the picomolar range) associated with each region of the array.

An alternative approach to robotic spotting uses an array of pins or capillary dispensers dipped into the wells, e.g., the 96 wells of a microtiter plate, for transferring an array of samples to a substrate. Arrays can also be fabricated by coating elements such as beads or optical fibers with samples to form target elements. U.S. Pat. No. 5,830,645 (issued Nov. 3, 1998 to Pinkel et al.) describes the use of beads to produce a polynucleotide array, and U.S. Pat. No. 5,690,894 (issued on Nov. 25, 1997 to Pinkel et al.) discloses a polynucleotide array fabricated from optical fibers.

In another application, the polynucleotide pools of the invention are particularly useful for producing polynucleotides intended for use as driver in subtractive hybridization protocols. Such protocols typically require large amounts (generally tens of micrograms) of driver. This requirement makes it difficult to examine differential expression of mRNAs present in a biological material that is available in small supply. This difficulty has been addressed by cloning the polynucleotide collections of interest prior to subtraction, so that the cloning vector is used to amplify the amount of polynucleotide available for hybridization. However, because subtraction requires previous cloning, it is complicated, suffers from under- and over-representation of sequences depending on differences in growth rates in the mixed population, and may risk recombination among sequences during propagation of the mixed population.

The methods of the present invention circumvent these problems by allowing production of large amounts of aRNA from limited amounts of polynucleotides, without the need for previous cloning. These methods are superior to PCR, which produces both sense and anti-sense strands that must be separated before use in subtractive hybridization. High- or low-abundance aRNA produced as described above can be used in methods of detecting and isolating polynucleotides that vary in abundance among different populations, for example, allowing mRNA expression to be compared among different tissues or within the same tissue according to physiologic state.

Anti-sense RNA also has a wide variety of uses in both analytical research and therapeutics. Anti-sense RNA functions in several prokaryotic systems to regulate gene expression. Similarly, anti-sense RNA can regulate the expression of many eukaryotic genes. This permits blocking expression of undesirable genes. Therapeutic use of anti-sense RNA therefore involves in vitro synthesis of anti-sense RNA with subsequent introduction into cells or the subject (see, generally, Melton, Antisense RNA and DNA, Cold Spring Harbor (1988).

In some applications, it is advantageous to stabilize the polynucleotides described herein or to produce polynucleotides that are modified to better adapt them for particular applications. To this end, the polynucleotides of the invention can contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2$—NH—O—$CH_2$, $CH_2$—$N(CH_3)$—O—$CH_2$ (known as the methylene(methylimino) or MMI backbone) and $CH_2$—O—$N(CH_3)$—$CH_2$, $CH_2$—$N(CH_3)$—$N(CH_3)$—$CH_2$, and O—$N(CH_3)$—$CH_2$—CH backbones (where phosphodiester is O—P—O—$CH_2$). Also preferred are polynucleotides having morpholino backbone structures. Summerton, J. E. and Weller, D. D., U.S. Pat. No. 5,034,506. Other preferred embodiments use a protein-nucleic acid or peptide-nucleic acid (PNA) backbone, wherein the phosphodiester backbone of the polynucleotide is replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Polynucleotides of the invention can contain alkyl and halogen-substituted sugar moieties and/or can have sugar mimetics such as cyclobutyls in place of the pentofuranosyl group. In other preferred embodiments, the polynucleotides can include at least one modified base form or "universal base" such as inosine. Polynucleotides can, if desired, include an RNA cleaving group, a cholesteryl group, a reporter group, an intercalator, a group for improving the pharmacokinetic properties of the polynucleotide, and/or a group for improving the pharmacodynamic properties of the polynucleotide.

Kits

The materials for use in the methods of the present invention are ideally suited for preparation of kits produced in accordance with well-known procedures. In one embodiment, a kit of the invention includes: (1) an antisense primer complex including an antisense primer linked to an RNA promoter sequence, wherein the RNA promoter sequence is 5' of the antisense primer; (2) a sense primer; and (3) instructions for performing a method of the invention. While the instructional materials typically comprise written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media can include addresses to internet sites that provide such instructional materials. Preferred kits include one or more of the various reagents (typically in concentrated form) utilized in the methods, including, for example, one or more buffers, the appropriate nucleotide triphosphates (e.g., dATP, dCTP, dGTP and dTTP; or rATP, rCTP, rGTP and UTP), reverse transcriptase, DNA polymerase, and/or RNA polymerase.

In another embodiment, a kit of the invention includes: (1) a selected polynucleotide pool of the invention, (2) an antisense primer complex as described above, and (3) a sense primer. This kit is useful for preparing amplified DNA from the selected polynucleotide pool. Preferred kits include one or more containers, each with one or more reagents for amplifying DNA, e.g., a buffer, nucleotide triphosphates and/or a DNA polymerase.

In yet another embodiment, a kit includes: (1) a selected polynucleotide pool of the invention, and (2) an RNA polymerase capable of transcribing aRNA from the selected polynucleotide pool. Preferred kits include one or more containers, each with one or more reagents for producing aRNA, e.g., a buffer and/or nucleotide triphosphates.

All publications cited herein are explictly incorporated by reference.

EXAMPLES

The following examples are offered to illustrate, but not to limit the claimed invention.

Example 1

Production of cDNA Enriched in Low-Abundance Sequences from Human Placental mRNA A. Synthesis of First-Strand cDNA and PCR 1. Universal PCR Anchor Added by Template-Switching First-strand cDNA was synthesized from human placental polyA+ RNA using a random primer linked to a T7 promoter sequence (Random-T7 primer): 5'-AAT-TCT-AAT-ACG-ACT-CAC-TAT-AGG-GNN-NN-NN-3'(N=A,T,C or G; SEQ ID NO:2). Briefly, a 5-μl cDNA synthesis mixture containing 1 μl human placenta polyA+ RNA (1 μg), 1 μl Random-T7 primer (20 μM), 1 μl PCR anchor Oligo (also called Template-Switching Oligo: 5-TGC-TGC-GAG-AAG-ACG-ACA-GAA-GGG-3', (the 3' "GGG" shown in bold were ribonucleotides; SEQ ID NO:3), and 2 μl of deionized H$_2$O. The mixture was incubated at 72° C. for 2 min and then 37° C. for 2 min. The volume was then adjusted to 10 μl with the following reagents: 2 μl of 5× first-strand synthesis buffer (250 mM Tris-HCl, pH8.3; 30 mM MgCl$_2$; and 375 mM KCl), 0.5 μl of dithiothreitol (DTT; 50 mM), 1 μl of dNTP mix (10 mM each DATP, dCTP, dGTP, dTTP), 0.5 μl Rnasin (20 units, Promega), and 1 μl (200 units) of MMLV reverse transcriptase (SuperscriptII™, Life Technologies). The reverse transcription was carried out at 42° C. for 90 min. The reaction was terminated by placing the tube on ice.

First-strand cDNA was diluted to about 1 pg/μl (about 1×10$^{-6}$) to eliminate rare transcripts, followed by PCR amplification in a 100 μl reaction containing 40 mM Tricine-KOH, pH9.2; 15 mM KOAc; 3.5 mM Mg(OAc)$_2$; and 0.2 μM 5'-'anchor primer (5'-TGC-TGC-GAG-AAG-ACG-ACA-GAA-3', SEQ ID NO:4); 0.2 μM Random-T7 primer; 0.2 mM each of dATP, dGTP, dCTP and dTTP; and 2 μl of Advantage™ cDNA Polymerase Mix (50×; contains KlenTaq-1 and Deep Vent polymerases; Clontech). PCR was carried out in a DNA Thermal Cycler 480 (PE Biosystems) using the following cycling conditions: 95° C. for 1 min; 30–35 cycles at 95° C. for 15 sec; 62° C. for 30 sec; and 72° C. for 6 min.

After PCR, double-stranted cDNA was purified by passing it over an S-200 spin column (Clontech). Before antisense RNA driver synthesis, the double-stranded cDNA was tested for amplification of glucose 3-phosphate dehydrogenase (G3PDH) and c-myc genes. After 25 cycles of PCR amplification, G3PDH was visible as an intense band on a 1.1% agarose gel stained with ethidium bromide. c-myc was not detectable on an ethidium bromide-stained gel, even after 35 cycles of amplification.

2. Universal PCR Anchor Added by Homopolymeric Tailing

First-strand cDNA was synthesized on human placenta polyA+ RNA using the Random-T7 primer of Method 1. Briefly, a 5 μt cDNA synthesis mixture containing 1 μl human placental polyA+ RNA (1 μg), 1 μl Random-T7 primer (20 μM), and 3 μl of deionized H$_2$O were incubated at 72° C. for 2 min and then 37° C. for 2 min. The volume was then adjusted to 10 μl with the following reagents: 2 μl of 5× first-strand synthesis buffer (250 mM Tris-HCl, pH8.3; 30 mM MgCl$_2$; and 375 mM KCl), 0.5 μl of DTT (50 mM), 1 μl of dNTP mix (10 mM each dATP, dCTP, dGTP, dTTP), 0.5 μl Rnasin (20 units, Promega) and 1 μl (200 units) of MMLV reverse transcriptase (SuperscriptII™, Life Technologies). The reverse transcription was carried out at 42° C. for 90 min. The reaction was terminated by placing the tube on ice.

Homopolymeric tailing was carried out as previously reported (D. J. Bertioli et al., BioTechnology, 1994) with following modifications. 20 μl of deionized H$_2$O was added to the first-strand cDNA mixture. The diluted first-stand cDNA mixture was purified using a CHROMA SPIN-100 column (Clontech) to eliminate primers and dNTPs as well as small cDNA fragments. Oligo-dC tailing was carried out by mixing the following: 30 μl purified first-strand cDNA; 1 μl 5× tailing buffer (0.5 M potassium cacodylate, pH7.2, 10 mM CoCl$_2$, 1 mM DTT ), 1 μl of 1 mM dCTP, 1 μl terminal transferase (15 units/μl; Life Technologies), 8 μl deionized H$_2$O (final volume was 50 μl). The reaction mixture was incubated at 37° C. for 1 h, followed by phenol/chloroform extraction and precipitation.

The Oligo-dC-tailed cDNA was diluted to about 10 pg/µl (about 1×10$^{-5}$) to eliminate rare transcripts, followed by PCR amplification in a 100 µl reaction containing 40 mM Tricine-KOH, pH9.2; 15 mM KOAc; 3.5 mM Mg(OAc)$_2$; and 0.2 µM 5'-dG$_{12}$ primer (5'-d(G)$_{12}$-VN-3', N=A, G, C, or T; V=A, G or C); 0.2 µM Random-T7 primer, 0.2 mM each of dATP, dGTP, dCTP and dTTP; and 2 µl of Advantage™ cDNA Polymerase Mix (5×; contains KlenTaq-1 and Deep Vent polymerases; Clontech). PCR was carried out in a DNA Thermal Cycler 480 (PE Biosystems) using following cycling conditions: 95° C. for 1 min.; 30–35 cycles at 95° C. for 15 sec; 52° C. for 30 sec; and 72° C. for 6 min.

After PCR, double-stranded cDNA was purified by passing passing it over an S-200 spin column (Clontech). Before antisense RNA driver synthesis, the double-stranded cDNA was tested for amplification of the (G3PDH) and c-myc genes. After 25 cycles of PCR amplification, G3PDH was visible as an intense band on a 1.1% agarose gel stained with ethidium bromide. c-myc was not detectable on an ethidium bromide-stained gel, even after 35 cycles of amplification.

B. Antisense RNA Synthesis

Antisense RNA was synthesized by mixing the following: the above double-stranded cDNA (1 µg); 5× RNA translation buffer (200 mM Tris-HCl, pH8.5; 60 mM MgCl$_2$; 350 mM KCl; 25 mM DTT; 2.5 mM ITP; 7.5 mM GTP; 10 mM ATP; 10 mM UTP; 10 mM CTP), 40 units of RNasin (Promega), and 80 units of T7 RNA polymerase (Boehringer Mannheim) were then added. H$_2$O was added to a final reaction volume of 50 µl. The mixture was incubated at 41° C. for 90 min. 10 units of DNase I (RNase free; Boehringer Mannheim) were then added. This reaction was incubated at 37° C. for 15 min, followed by phenol/chloroform extraction and precipitation.

C. Subtractive Hybridization

Subtractive hybridization was performed using the above human placenta aRNA (enriched in high-abundance sequences) as a "driver" and normal human placenta mRNA (same origin as aRNA) as "tester." Table 1 lists the various amounts of aRNA and placental mRNA in each reaction mixture.

TABLE 1

The Ratio of aRNA and mRNA for Subtractive Hybridization

| Sample | A | B | C | D |
|---|---|---|---|---|
| Placental mRNA | 1 µg(1 µl) | 1 µg(1 µl) | 1 µg(1 µl) | 1 µg(1 µl) |
| Placetal aRNA | Omitted | 0.5 µg(0.5 µl) | 1 µg(1 µl) | 2 µg(2 µl) |
| DEPC H$_2$O | 2 µl | 1.5 µl | 1 µl | Omitted |
| Total | 3 µl | 3 µl | 3 µl | 3 µl |

After mixing, the tubes were incubated in a PE 9600 Thermal Cycler at 68° C. for 20 min. The temperature was then increased to 45° C. for a 16 h incubation.

D. cDNA Synthesis

Samples A, B, C, and D (above) were used as templates for first-strand cDNA synthesis using an Oligo-d(T)$_{30}$ primer (5'-d(T)$_{30}$-VN-3', N=A, G, C, or T; V=A, G or C). Briefly, 2 µl 10 mM Oligo-d(T)$_{30}$ was added to each sample, followed by incubation at 72° C. for 2 min. The reaction mixtures were then immediately transferred to an ice water bath for 2 min. The volume was adjusted to 10 µl with the following reagents: 2 µl of 5× first-strand synthesis buffer (250 mM Tris-HCl, pH8.3; 30 mM MgCl$_2$, and 375 mM KCl), 0.5 µl of DTT (50 mM), 1 µl of dNTP mix (10 mM each dATP, dCTP, dGTP, dTTP), 0.5 µl Rnasin (20 units, Promega) and 1 µl (200 units) of MMLV reverse transcriptase (SuperscriptII™, Life Technologies). The reverse transcription was carried out at 42° C. for 90 min. The reactions were terminated by placing the tubes on ice.

E. Oligo-dG Tailing

After first-strand synthesis, RNA was degraded by adding 1 µl of 100 mM NaOH to each first-strand synthesis mixture and incubating at 68° C. for 30 min. 19 µl of deionized H$_2$O was then to each first-strand mixture, and DNA was purified using a Chroma Spin 100™ column (Clontech). Oligo-dG tailing was carried out by mixing the following: 30 µl purified first-strand cDNA; 1 µl 5× tailing buffer (0.5 M potassium cacodylate, pH7.2, 10 mM CoCl$_2$, 1 mM DTT), 1 µl of 1 mM dGTP, 1 µl terminal transferase (15 units/µl; Life Technologies), 8 µl deionized H$_2$O (final volume was 50 µl). The reaction mixtures were incubated at 37° C. for 1 h, followed by phenol/chloroform extraction and precipitation.

F. Double-Stranded cDNA Synthesis by Low-Cycle PCR and Analysis of PCR Products 1. 0.9 kb Placental Transcript:

The subtraction of low-abundance sequences in samples A–D was assayed by examining the level of cDNA corresponding to a 0.9 kb placental "housekeeping" transcript. Low-cycle PCR amplification was carried out by dissolving the pellet obtained in the previous step in a 100 µl reaction containing 40 mM Tricinc-KOH, pH9.2; 15 mM KOAc; 3.5 mM Mg(OAc)$_2$; and 0.2 µM 5'-dC$_{12}$ primer (5'-d(C)$_{12}$-VN-3', N=A, G, C, or T; V=A, G or C); 0.2 µM Oligo-d(T)$_{30}$; 0.2 mM each of dATP, dGTP, dCTP and dTTP; and 2 µl of Advantage™ cDNA Polymerase Mix (50×; contains KlenTaq-1 and Deep Vent polymerases; Clontech). PCR was carried out in a DNA Thermal Cycler 480 (PE Biosystems) using following cycling conditions: 95° C. for 1 min; 8 cycles at 95° C. for 15 sec; 52° C. for 30 sec; and 72° C. for 6 min.

PCR products from samples A, B, C and D were loaded onto a 1.1% agarose gel (5 µl/well), along with 200 ng 1 kb DNA ladder (Life Technologies). Staining with ethidium bromide revealed that the banding profile varied with the ratio of antisense mRNA driver to placental mRNA. Specifically, the intensity of a band at 0.9 kb corresponding to a human placental housekeeping gene decreased with increasing ratio of aRNA/mRNA, and was nearly undetectable in sample D, indicating that aRNA driver hybridizes to high-abundance mRNA sequences and subtracts them.

2. Glucose 3-Phosphate Dehydrogenase (G3PHD):

The subtraction of high-abundance sequences in samples A–D was also assayed by examining the level of cDNA corresponding to the housekeeping gene G3PHD. Samples A, B, C and D were each PCR-amplified in a 50 µl reaction mixture containing 40 mM Tricine-KOH, pH9.2; 15 mM KOAc; 3.5 mM Mg(OAc)$_2$; and 0.2 µM 5' and 3'G3PHD Amplimer set (Clontech); 0.2 mM each of dATP, dGTP, dCTP and dTTP; and 2 µl of Advantage™ cDNA Polymerase Mix (50×; contains KlenTaq-1 and Deep Vent polymerases; Clontech). PCR was carried out in a DNA Thermal Cycler 480 (PE Biosystems) using following cycling conditions: 95° C. for 1 min; 25 cycles at 95° C. for 15 sec; 68° C. for 2 min.

PCR products from samples A, B, C and D were loaded onto a 1.1% agarose gel (5 µl/well), along with 200 ng 1 kb DNA ladder (Life Technologies). Staining with ethidium bromide revealed that the intensity of the band corresponding to the housekeeping gene G3PHD decreased with increasing ratio of aRNA/mRNA and was nearly undetectable in sample D, confirming that aRNA driver subtracts high-abundance mRNA sequences.

3. c-myc:

The c-myc gene was used as a marker to assay the enrichment of low-abundance sequences in samples A–D. Each sample was PCR-amplified as described in the G3PHD study except that the 5' and 3' c-myc Amplimer set (Clontech) were used as primers, and PCR was carried out on using following cycling conditions: 95° C. for 1 min; then 30 cycles at 95° C. for 15 sec; and 68° C. for 2 min.

PCR products from samples A, B, C and D were loaded onto a 1.1% agarose gel (5 μl/well), along with 200 ng 1 kb DNA ladder (Life Technologies). Staining with ethidium bromide revealed that the intensity of c-myc amplicon increased with increasing ratio of aRNA/mRNA. The results indicate that c-myc was present in the normal human placental RNA, but not in the aRNA driver, and that subtractive hybridization, followed by amplification, produces a polynucleotide pool enriched in low-abundance sequences, such as c-myc.

Example 2

Production of cDNA Enriched in Low-Abundance Sequences from mRNA Prepared from Various Tissues To test reproducibility of the methods of the invention, aRNA driver was produced from human brain, fetal brain, liver, and kidney mRNAs, as described in Example 1. An mRNA sample from each tissue was subjected to subtractive hybridization with aRNA driver prepared from the same tissue (group A). Negative controls (i.e., not treated with aRNA) were included for each sample (group B). After subtraction, low-cycle PCR was carried out to generate double-stranded cDNAs corresponding to unhybridized mRNA sequences.

The P50 gene was used as a marker to assay the enrichment of low-abundance sequences. Each sample was amplified in a 50 μl reaction containing 40 mM Tricine-KOH, pH9.2; 15 mM KOAc; 3.5 mM Mg(OAc)$_2$; and 0.2 μM 5' and 3' P50 Amplimer set (Clontech); 0.2 mM each of dATP, dGTP, dCTP and dTTP; and 2 μl of Advantage™ cDNA Polymerase Mix (50×; contains KlenTaq-1 and Deep Vent polymerases; Clontech). PCR was carried out in a DNA Thermal Cycler 480 (PE Biosystems) using following cycling conditions: 95° C. for 1 min; 30 cycles at 95° C. for 15 sec; and 68° C. for 2 min.

Analysis of the PCR products by electrophoresis on a 1.1% agarose gel, followed by staining with ethidium bromide revealed that group A samples (enriched for low-abundance sequences) contained P50 sequences, whereas group B samples (negative control) contained no detectable P50 sequences. The results indicate that the methods of the invention are effective for producing selected polynucleotide pools, regardless of tissue type.

Example 3

Production of cDNA Enriched in Low-Abundance Sequences of Varying Length from mRNA Prepared from Human Testis mRNA To test for enrichment of low-abundance sequences of varying length, aRNA driver was produced from human testis mRNAs, as described in Example 1. A human testis mRNA sample was subjected to subtractive hybridization with the aRNA driver (to generate a group A sample). A negative control (i.e., not treated with aRNA) was included (to generate a group B sample). After subtraction, low-cycle PCR was carried out to produce double-stranded cDNAs corresponding to unhybridized mRNA sequences.

Interleukin-6 (IL6, 0.6 kb ORF fragment), P50 (2.8 kb ORF), and Insulin Growth Factor Receptor (IGFR; 4.8 kb ORF fragment) were used as markers to check low-abundance gene enrichment and size representation. A and B samples were PCR-amplified in a 50 μl reaction containing 40 mM Tricine-KOH, pH9.2; 15 mM KOAc; 3.5 mM Mg(OAc)$_2$; and 0.2 μM 5' and 3' IL6-, P50-, or IGFR-specific primer set; 0.2 mM each of dATP, dGTP, dCTP and dTTP; and 2 μl of Advantage™ cDNA Polymerase Mix (50×; contains KlenTaq-1 and Deep Vent polymerases; Clontech). PCR was carried out in a DNA Thermal Cycler 480 (PE Biosystems) using following cycling conditions: 95° C. for 1 min; 30 cycles at 95° C. for 15 sec; and 68° C. for 5 min.

Analysis of the PCR products by electrophoresis on a 1.1% agarose gel, followed by staining with ethidium bromide, revealed that group A samples (enriched for low-abundance sequences) contained bands corresponding to IL6, P50, and IGFR sequences, whereas group B samples (negative control) contained no detectable bands corresponding to these sequences. The results indicate that the methods of the invention enrich for low-abundance transcripts of varying sizes.

---

What is claimed is:

1. A method for preparing a selected polynucleotide pool from a polynucleotide sample comprising:
   a) synthesizing first antisense polynucleotide strands from sense polynucleotides of, or prepared from, the polynucleotide sample, wherein said first antisense polynucleotide strands are synthesized using an antisense primer complex comprising an antisense primer operably linked to an RNA promoter sequence, wherein the RNA promoter sequence is 5' of the antisense primer;
   b) adding a universal primer site to the 3' ends of the first antisense polynucleotide strands;
   c) diluting the first antisense polynucleotide strands to substantially eliminate at least some low-abundance first antisense polynucleotide strands; and
   d) producing first double-stranded polynucleotides from the remaining first antisense polynucleotide strands, wherein the first double-stranded polynucleotides are enriched in high-abundance polynucleotide sequences relative to the polynucleotide sample.

2. The method of claim 1 wherein the polynucleotide sample is an mRNA sample, the first antisense polynucleotide strands are first antisense cDNA strands, and the first double-stranded polynucleotides are first double-stranded cDNA molecules.

3. The method of claim 2 wherein the synthesis of first antisense cDNA strands is primed using a random primer or an oligonucleotide-dT primer.

4. The method of claim 2 wherein the universal primer site is added to the 3' end of the first antisense cDNA strands by template switching, oligonucleotide-tailing, or ligation.

5. The method of claim 1 wherein the RNA promoter sequence is an RNA promoter sequence recognized by a bacteriophage RNA polymerase selected from the group consisting of T7, T3, and SP6.

6. The method of claim 1 wherein the first double-stranded polynucleotides are produced by amplifying the remaining first antisense polynucleotide strands, and wherein the amplification is carried out using a universal primer that hybridizes to the universal primer site as the 5' primer and using the antisense primer complex as the 3' primer.

7. The method of claim 6 wherein the amplification is performed by enhanced polymerase chain reaction.

8. The method of claim 1 wherein the first double-stranded polynucleotides are produced using an enzyme mixture comprising a DNA polymerase, a DNA ligase, and an RNase.

9. The method of claim 1 further comprising synthesizing first antisense RNA molecules from the first double-stranded polynucleotides.

10. The method of claim 9 further comprising:
   a) contacting the first antisense RNA molecules to sense polynucleotide strands of, or prepared from, the polynucleotide sample under hybridization conditions to form a hybridization mixture, thereby producing unhybridized sense polynucleotide strands that are enriched in low-abundance polynucleotide sequences relative to the polynucleotide sample;
   b) synthesizing second antisense polynucleotide strands from the unhybridized sense polynucleotide strands using an antisense primer or an antisense primer complex, said antisense primer complex comprising an antisense primer operably linked to an RNA promoter sequence, wherein the RNA promoter sequence is 5' of the antisense primer;
   c) adding a universal primer site to the 3' ends of the second antisense polynucleotide strands; and
   d) producing second double-stranded polynucleotides from the second antisense polynucleotide strands.

11. The method of claim 10 wherein the molar ratio of the first antisense RNA molecules to the other polynucleotides in the hybridization mixture is between about 1 and about 100 to 1.

12. The method of claim 10 wherein the polynucleotide sample is an mRNA sample, the sense polynucleotide strands are the mRNA molecules in the mRNA sample, the second antisense polynucleotide strands are second antisense cDNA strands, and the second double-stranded polynucleotides are second double-stranded cDNA molecules.

13. The method of claim 12 wherein the synthesis of second antisense cDNA strands is primed using oligonucleotide-dT priming.

14. The method of claim 12 wherein the universal primer site is added to the 3' end of the second antisense cDNA strands by template switching, oligonucleotide-tailing, or ligation.

15. The method of claim 10 wherein the second antisense polynucleotide strands are synthesized from the unhybridized sense polynucleotide strands using an antisense primer complex, and the RNA promoter sequence of (b) comprises an RNA promoter sequence for an RNA polymerase selected from the group consisting of T7, T3, and SP6.

16. The method of claim 10 wherein the second double-stranded polynucleotides are produced by amplifying the second antisense polynucleotide strands, and wherein the amplification is carried out using a universal primer that hybridizes to the universal primer site as the 5' primer and using the antisense primer or antisense primer complex as the 3' primer.

17. The method of claim 16 wherein the amplification is performed by enhanced polymerase chain reaction.

18. The method of claim 10 wherein the second double-stranded polynucleotides are produced using an enzyme mixture comprising a DNA polymerase, a DNA ligase, and an RNase.

19. The method of claim 10 wherein the universal primer and/or the antisense primer or antisense primer complex each comprise a restriction site.

20. The method of claim 10 further comprising cloning at least one of the second double-stranded polynucleotides into a vector.

21. The method of claim 20 wherein the cloned double-stranded polynucleotides encode a polypeptide, and the vector is an expression vector.

22. The method of claim 21 further comprising introducing the expression vector into a host cell and expressing the protein encoded by the cloned double-stranded polynucleotide.

23. The method of claim 10 wherein the second antisense polynucleotide strands are synthesized from the unhybridized sense polynucleotide strands using an antisense primer complex, said method further comprising synthesizing antisense RNA molecules from the second double-stranded polynucleotides.

24. The method of claim 10 comprising employing second double-stranded polynucleotides or a polynucleotide produced directly or indirectly therefrom in a hybridization reaction.

25. The method of claim 24 wherein at least one of the second double-stranded polynucleotides or a polynucleotide produced therefrom is labeled with a detectable label.

26. The method of claim 10 further comprising attaching a plurality of the second double-stranded polynucleotides or polynucleotides produced therefrom to a substrate to produce a polynucleotide array.

27. The method of claim 10 further comprising amplifying one or more of the second double-stranded polynucleotides.

28. The method of claim 27 wherein said one or more double-stranded polynucleotides are amplified using one or more gene-specific primers.

29. A method for preparing a selected polynucleotide pool from a polynucleotide sample comprising:
   a) hybridizing first antisense polynucleotide strands to sense polynucleotide strands, wherein the first antisense polynucleotide strands are prepared from a first polynucleotide sample and are enriched in high-abundance polynucleotide sequences relative to the first polynucleotide sample, and wherein the sense polynucleotide strands are of, or prepared from, a second polynucleotide sample, said hybridization producing unhybridized sense polynucleotide strands that are enriched in low-abundance polynucleotide sequences relative to the second polynucleotide sample; and
   b) synthesizing second antisense polynucleotide strands from the unhybridized sense polynucleotide strands using an antisense primer or an antisense primer complex, said antisense primer complex comprising an antisense primer operably linked to an RNA promoter sequence, wherein the RNA promoter sequence is 5' of the antisense primer;
   c) adding a universal primer site to the 3' ends of the second antisense polynucleotide strands;
   d) producing double-stranded polynucleotides from the second antisense polynucleotide strands.

30. The method of claim 29 wherein the molar ratio of the first antisense polynucleotide strands to the other polynucleotides in the hybridization mixture is between about 1 and about 100 to 1.

31. The method of claim 29 wherein the polynucleotide first and second sample samples are mRNA samples, the sense polynucleotide strands are the mRNA molecules, the first antisense polynucleotide strands are antisense RNA, the second antisense polynucleotide strands are antisense cDNA strands, and the double-stranded polynucleotides are double-stranded cDNA molecules.

32. The method of claim 29 wherein the double-stranded polynucleotides are produced by amplifying the second antisense polynucleotide strands, and wherein the amplification is carried out using a universal primer that hybridizes to the universal primer site as the 5' primer and using the antisense primer or antisense primer complex as the 3' primer.

33. The method of claim 29 wherein the universal primer and/or the antisense primer or antisense primer complex each comprise a restriction site.

34. The method of claim 29 further comprising cloning at least one of the double-stranded polynucleotides into a vector.

35. The method of claim 34 wherein the cloned polynucleotide encodes a polypeptide, and the vector is an expression vector.

36. The method of claim 35 further comprising introducing the expression vector into a host cell and expressing the protein encoded by the cloned double-stranded polynucleotide.

37. The method of claim 29 wherein the second antisense polynucleotide strands are synthesized from the unhybridized sense polynucleotide strands using an antisense primer complex, said method further comprising synthesizing antisense RNA molecules from the double-stranded polynucleotides.

38. The method of claim 29 comprising employing one or more of the double-stranded polynucleotides or a polynucleotide produced directly or indirectly therefrom in a hybridization reaction.

39. The method of claim 38 wherein at least one of the double-stranded polynucleotides or a polynucleotide produced therefrom is labeled with a detectable label.

40. The method of claim 29 further comprising attaching a plurality of the double-stranded polynucleotides or polynucleotides produced therefrom to a substrate to produce a polynucleotide array.

41. The method of claim 29 further comprising amplifying at least one of the double-stranded polynucleotides.

42. The method of claim 41 wherein said one or more double-stranded polynucleotides are amplified using one or more gene-specific primers.

43. The method of claim 29 wherein the first and second polynucleotide samples are different samples.

44. A plurality of polynucleotides prepared from a polynucleotide sample, wherein the plurality of polynucleotides includes at least $10^3$ polynucleotides with different sequences and is substantially enriched in high-abundance polynucleotide sequences relative to the polynucleotide sample, wherein the polynucleotides each comprise a RNA promoter sequence and a universal primer site.

45. A plurality of polynucleotides prepared from a polynucleotide sample, wherein the plurality of polynucleotides includes at least $10^3$ polynucleotides with different sequences and is substantially enriched in low-abundance polynucleotide sequences relative to the polynucleotide sample, wherein the polynucleotides each comprise a RNA promoter sequence and a universal primer site.

46. The plurality of polynucleotides of claim 45 wherein the polynucleotides are double-stranded cDNA.

47. A plurality of polynucleotides prepared from a polynucleotide sample, wherein the plurality of polynucleotides includes at least $10^3$ polynucleotides with different sequences and is substantially enriched in low-abundance polynucleotide sequences relative to the polynucleotide sample, wherein the polynucleotides are antisense RNA.

48. A kit comprising:
   a) the plurality of polynucleotides of claim 44;
   b) an antisense primer complex comprising a antisense primer operably linked to an RNA promoter sequence, wherein the RNA promoter sequence is 5' of the antisense primer; and
   c) a sense primer.

49. A kit comprising:
   a) the plurality of polynucleotides of claim 44; and
   b) an RNA polymerase capable of transcribing antisense RNA from the plurality of polynucleotides.

50. A method for preparing a selected polynucleotide pool from a polynucleotide sample comprising:
   a) synthesizing first antisense polynucleotide strands from sense polynucleotides of, or prepared from, the polynucleotide sample;
   b) diluting the first antisense polynucleotide strands to substantially eliminate at least some low-abundance first antisense polynucleotide strands; and
   c) producing first double-stranded polynucleotides from the remaining first antisense polynucleotide strands, wherein the first double-stranded polynucleotides are enriched in high-abundance polynucleotide sequences relative to the polynucleotide sample;
   d) producing second antisense polynucleotide strands from the first double-stranded polynucleotides;
   e) contacting the second antisense polynucleotide strands with sense polynucleotide strands, wherein the sense polynucleotide strands are of, or prepared from, the polynucleotide sample, wherein said contacting is carried out under hybridization conditions to form a hybridization mixture, thereby producing unhybridized sense polynucleotide strands that are enriched in low-abundance polynucleotide sequences relative to the polynucleotide sample;
   f) synthesizing third antisense polynucleotide strands from the unhybridized sense polynucleotide strands;
   g) producing second double-stranded polynucleotides from the third antisense polynucleotide strands.

* * * * *

SEQUENCE LISTING

<160> NUMBER OF SEQ ID NOS: 4

<210> SEQ ID NO 1
<211> LENGTH: 25
<212> TYPE: DNA
<213> ORGANISM: Bacteriophage T7

<400> SEQUENCE: 1
aattctaata cgactcacta taggg                    25

<210> SEQ ID NO 2
<211> LENGTH: 31
<212> TYPE: DNA
<213> ORGANISM: Artificial Sequence
<220> FEATURE:
<223> OTHER INFORMATION: Random-T7 Primer

```
-continued
<221> NAME/KEY: misc_feature
<222> LOCATION: (26)..(31)
<223> OTHER INFORMATION: N = A, T, G, or C

<400> SEQUENCE: 2
aattctaata cgactcacta tagggnnnnn n                                    31

<210> SEQ ID NO 3
<211> LENGTH: 24
<212> TYPE: DNA
<213> ORGANISM: Artificial Sequence
<220> FEATURE:
<223> OTHER INFORMATION: Template-Switching Oligonucleotide

<400> SEQUENCE: 3
tgctgcgaga agacgacaga aggg                                            24

<210> SEQ ID NO 4
<211> LENGTH: 21
<212> TYPE: DNA
<213> ORGANISM: Artificial Sequence
<220> FEATURE:
<223> OTHER INFORMATION: 5'-Anchor Primer

<400> SEQUENCE: 4
tgctgcgaga agacgacaga a                                               21
```